United States Patent
Claudon et al.

(10) Patent No.: US 9,869,627 B2
(45) Date of Patent: Jan. 16, 2018

(54) DEVICE FOR MEASURING IMPERMEABILITY OF THE SEALING MEANS OF A FILTER CARTRIDGE AND PROCESS THEREOF

(71) Applicant: General Electric Company, Schenectady, NY (US)

(72) Inventors: Philippe Claudon, Belfort (FR); Ludovic Pesenti, Belfort (FR)

(73) Assignee: General Electric Company, Schenectady, NY (US)

( * ) Notice: Subject to any disclaimer, the term of this patent is extended or adjusted under 35 U.S.C. 154(b) by 523 days.

(21) Appl. No.: 13/949,791

(22) Filed: Jul. 24, 2013

(65) Prior Publication Data

US 2014/0026643 A1 Jan. 30, 2014

(30) Foreign Application Priority Data

Jul. 24, 2012 (FR) .................................... 12 57161

(51) Int. Cl.
*G01N 15/08* (2006.01)
*G01M 3/28* (2006.01)
*G01M 13/00* (2006.01)

(52) U.S. Cl.
CPC .......... *G01N 15/08* (2013.01); *G01M 3/2869* (2013.01); *G01M 13/005* (2013.01); *B01D 2273/18* (2013.01)

(58) Field of Classification Search
CPC ............. G01M 3/2869; G01M 13/005; B01D 2273/18; G01N 2015/0846; G01N 15/08
USPC .................... 73/38, 159, 865.9, 866
See application file for complete search history.

(56) References Cited

U.S. PATENT DOCUMENTS

| | | | |
|---|---|---|---|
| 3,400,580 A | 9/1968 | Haren et al. | |
| 3,974,937 A | 8/1976 | Eaton | |
| 4,765,810 A | 8/1988 | Wetzel | |
| 6,591,662 B1 | 7/2003 | Grimard et al. | |
| 2010/0180670 A1 | 7/2010 | Yung et al. | |

FOREIGN PATENT DOCUMENTS

| | | | | |
|---|---|---|---|---|
| DE | 3126089 A1 | 1/1983 | | |
| DE | 9105501 U1 | 7/1991 | | |
| DE | 10011940 A1 | 9/2001 | | |
| EP | 2090875 A2 * | 8/2009 | ............ | G01M 3/223 |
| WO | 0002432 A2 | 1/2000 | | |

OTHER PUBLICATIONS

Non Patent Literature "Gasket Sealing", accessed at http://web.archive.org/web/20110418042641/http://www.sensorprod.com/glossary/gasketsealing/gasketsealing.php, archived on Apr. 18, 2011.*
European Standard DIN EN 1886—Ventilation for Buildings Air Handling Units Mechanical Performance, May 1998, 29 pages.
Search Report and Written Opinion from PCT/2013/051825 dated Oct. 22, 2013.

* cited by examiner

Primary Examiner — Daniel S Larkin
Assistant Examiner — Irving A Campbell
(74) Attorney, Agent, or Firm — Barclay Damon LLP

(57) ABSTRACT

A device for measuring permeability of a filter cartridge seal includes a blocking member for blocking an input to the filter cartridge and a housing for tightening the seal. A removable chamber wall is configured to form a sealed chamber with the housing and the blocking member. Pressure in the sealed chamber is varied to test the seal and to detect leaks.

7 Claims, 2 Drawing Sheets

DEVICE FOR MEASURING IMPERMEABILITY OF THE SEALING MEANS OF A FILTER CARTRIDGE AND PROCESS THEREOF

CROSS-REFERENCE TO RELATED APPLICATIONS

This application claims priority to French Patent Application No: 1257161, filed Jul. 24, 2012, and entitled "Device for measuring impermeability of the sealing means of a filter cartridge and process thereof."

BACKGROUND OF THE INVENTION

The present invention concerns filters, in particular air filters. More particularly, the present invention concerns the characterization of filter cartridge seal impermeability, and more precisely impermeability to air.

Air filters are commonly used in industrial devices to separate gases from the particles they contain. The air filter may be used at the exit point of a device, to purify gases prior to release into the atmosphere; or at the entry point of a device to purify the air or gas used inside the device, for example at the entry point of a gas turbine compressor.

By design, air filters are built to separate particles from gas, retaining them in a manner comparable to a sieve. The filter's interstitial spaces block the passage of particles while still enabling gas or air to flow. However, the particles retained in the filter place limits on efficient filter volume; and cleaning or replacement of the filter becomes necessary following a certain amount of usage. Filters are thus built in the form of cartridges. The cartridges are equipped with sealing means comprising attachment means and one or several gasket seals, which enable easy and fast replacement of the filter when it is obstructed or congested.

However, in view of enabling proper function of the filter, it is also necessary to ensure that the filter cartridge and its sealing means are tight or impermeable to air or gas, to make sure that the circulating air or gas is effectively crossing the filter, and not taking a parallel path along which no filtration occurs.

BRIEF DESCRIPTION OF THE INVENTION

One of the purposes of the present invention is to characterize impermeability, in particular to air, of the sealing means of an air filter cartridge, as well as impermeability of the sealing means on the cartridge support.

According to the invention, a device for measuring impermeability is described, in particular to air, of the means of sealing the filter cartridge, comprising: means of obturating the cartridge, a housing suited to cooperate tightly with the sealing means of the cartridge, removable means of closure, suited to cooperate with the provided housing of the cartridge and the means of obturating it, in view of forming a sealed chamber, and means of fluid suction or injection mounted at one entry point of the means of closure, and capable of lowering or increasing the pressure inside the sealed chamber, in view of detecting leaks on the cartridge.

Thus, when the entry point of the cartridge is closed and when applying increased or lowered pressure to the cartridge, the device is able to highlight gas or liquid leaks, at cartridge level, depending on whether lowered or increased pressure is applied, and in particular at the level of the sealing means.

Preferably, the removable means of closure contain a pressure sensor. In this case, the device evaluates impermeability of the filter cartridge depending on changes in pressure level across time inside the sealed chamber.

Preferably, the removable means of closure also comprise a temperature sensor to measure the temperature of the fluid inside the sealed chamber, and more preferably two temperature sensors to measure ambient temperature and fluid temperature inside the sealed chamber. In this case, impermeability of the cartridge is analyzed as a function of fluid temperature, for example a gas, such as air, or a liquid.

Preferably, the measuring device comprises control means suited to determine changes in pressure levels, and optionally in temperature, inside the sealed chamber, depending on time, for example for a period of time ranging from 5 to 300 minutes, preferably from 30 to 240 minutes and more preferably from 60 to 180 minutes. The means of control may thus consist of a computer receiving as input the pressure measurements, and optionally the temperature measurements, and being suited to map the course of these measurements across time.

According to one embodiment, the cartridge presents an input, and an output, essentially parallel to the input, and a filter mounted between the input and the output. The filter is intended for mounting on the outside of the sealed chamber, and the means of air, or gas, suction or injection are suited for introducing a fluid under pressure inside the sealed chamber.

Preferably, the housing comprises a ridge suited to support the sealing means of the filter cartridge, and in which the device also contains a pressure sensitive film suitable for mounting between the ridge of the housing and the sealing means of the cartridge. Such a film enables to capture the spread/distribution of pressure forces occurring between the cartridge and the housing, in particular at the level of the gasket seal of the cartridge.

According to another embodiment of the invention, the cartridge comprises a first circular plate with an opening that defines an output section, a second circular plate attached at a distance from the first circular plate, and a filter with cylindrical symmetry mounted between the first plate and second plate. The filter is intended to be mounted inside the sealed chamber and the means of suction or injection are suited to lower pressure inside the sealed chamber.

Preferably, the device also comprises heating means suited to heat the fluid that is present or introduced inside the sealed chamber. According to another aspect, the invention also concerns a process for measuring impermeability, in particular to air, of the sealing means of a filter cartridge, wherein: a) the cartridge is assembled to a device according to one of the preceding claims, b) the obturating means are positioned at the entry point of the filter, or in place of at least a part of the filter, c) there are closing means on the housing in view of forming a sealed chamber, d) pressure is lowered or increased in the sealed chamber, and c) the change in pressure levels is measured across time, and optionally of the temperature, in the sealed chamber.

Preferably, prior to taking a measurement of the cartridge impermeability, a sealed wall is assembled with the device and the steps c) to e) are carried out in view of detecting leaks on the device measuring impermeability. Thus, it is possible to characterize the measuring device prior to using it with cartridge filters.

Preferably, the device comprises a support ridge for the filter cartridge, and prior to taking a measurement of cartridge impermeability; a pressure-sensitive film on contact is placed between the sealing means of the filter cartridge and the supporting ridge of the filter. Thus, it becomes possible to determine spread/distribution of the contact pressure exerted by the sealing means on the supporting ridge, and thus to determine the spread/distribution of the contact pressure exerted by the filter cartridge on its support, in particular at the level of the gasket seals.

Preferably, changes in pressure levels are measured and optionally of the temperature, inside the sealed chamber, for a period of time ranging from 5 to 300 minutes, preferably from 30 to 240 minutes and more preferably between 60 and 180 minutes.

BRIEF DESCRIPTION OF THE DRAWINGS

Other advantages and characteristics of the invention will appear clearly following a detailed description of two non-limiting embodiments of the invention and the appended drawings, wherein.

DETAILED DESCRIPTION OF THE INVENTION

Figure 1:
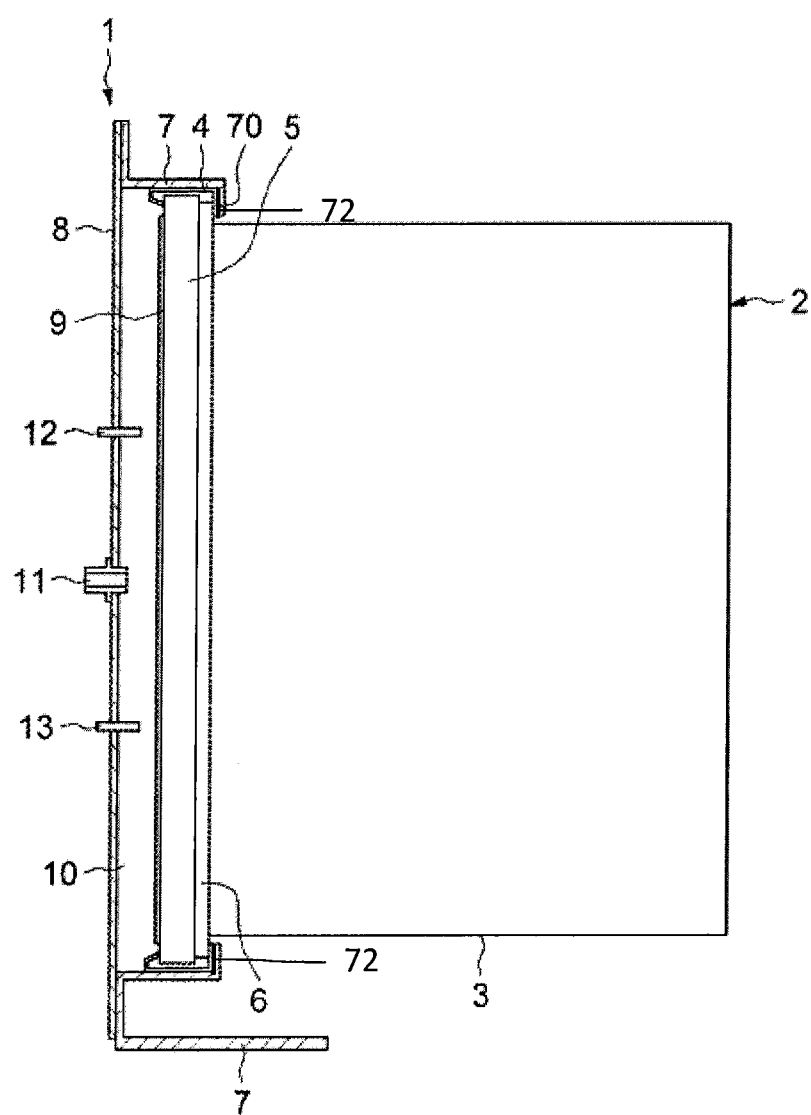
FIG. 1 schematically represents a section of the measuring device according to a first embodiment of the invention, suitable, for example, for testing of filters termed static.

FIG. 1 schematically represents a section of the measuring device 1 according to a first embodiment of the invention. The device 1 enables measurement of the impermeability of a filter cartridge 2, and in particular of the sealing means of cartridge 2.

The measuring device 1 is suited to cooperate with cartridge 2. Cartridge 2 comprises a casing, defining at both ends of the cartridge 2, an input and an output essentially parallel. The cartridge 2 also comprises an (unrepresented) filter mounted between the input and the output. The filter may for example be a static filter. The casing 3 may for example be cylindrical with two base surfaces forming the input and the output of the cartridge 2. The cartridge 2 comprises, within proximity of the entry point, for example on the circumference of the base surface forming the entry point, sealing mechanisms enabling to tightly mount, the filter cartridge 2 inside the final device. Thus, the sealing means also comprise attachment means 4 suitable for maintaining the cartridge 2 on a support, a ridge 5 forming an abutment for the support, and an gasket seal 6 on the ridge 5, suited for creating a seal between the support and ridge 5.

The measuring device 1 comprises a housing 7 suited to cooperate with the ridge 5 of the cartridge 2. The housing has a section similar to that of the casing 3 and comprises a supporting ridge 70. The ridge 5 of the filter cartridge 2 is thus held up by the attachment means 4, as an abutment against the supporting ridge 70 of the housing, in view of exerting pressure on the gasket seal 6 ensuring tightness between the measuring device 1 and the filter cartridge 2. The housing 7 of the measuring device 1 is similar to that of the final device for which filter cartridge 2 is intended, in view of enabling testing of the impermeability of cartridge 2 under conditions similar to those of final usage.

The measuring device 1 also comprises removable means of closure 8 and obturating means 9. The obturating means 9 are intended to close the filter cartridge 2, for example obstructing the entry of the filter or taking the place of at least a part of the filter, in view of enabling control of the pressure upstream from the cartridge 2. The removable means of closure 8 are suited to cooperate with housing 7, in a sealed manner, in view of forming, once the filter cartridge 2 is mounted in housing 7 with obturating means 9, a sealed chamber 10. For example, an (unrepresented) gasket seal may be mounted between housing 7 and the obturating means.

The removable means of closure 8 otherwise comprise an entry point 11 on which can be mounted suction or injection means of an (unrepresented) fluid (air or gas or liquid), for example a pump, in view of lowering or increasing the pressure inside the sealed chamber 10. The removable means of closure 8 may also comprise a temperature sensor 12 and/or a pressure sensor (13). The temperature sensor 12 enables to determine the temperature of the fluid present in the sealed chamber 10, and thus enables to characterize the impermeability of the cartridge 2 as a function of the fluid temperature. The pressure sensor 13 enables to determine changes across time of the pressure inside the sealed chamber 10.

In view of confirming the source of the leaks detected by the device 1, a sealed plate may be mounted in place of the cartridge 2, and test measurement of impermeability may be taken of the device itself. Such a measurement then enables to determine the impermeability of the measuring device 1 (in particular of the housing, the means of closure and the sensors), and thus to determine performance of the measuring device 1. As an example, an increase in pressure of 10 000 Pa may be applied for 2 hours, followed by an increase of 150 Pa, for two hours. In case of leakage, smoke or helium may be used to locate and quantify the leaks, in view of repairing them.

During a measurement of impermeability, the suction and injection means are used to augment pressure inside the sealed chamber 10. Then, the entry point 11 is closed and the pressure sensor measures pressure changes across time. The increased pressure added to the sealed chamber may be at least 10 000 Pa (100 mBar). More particularly, the increased pressure may vary depending on time : thus increased pressure of 4000 Pa for 15 minutes may be added, then 150 Pa for 15 minutes, then 2500 Pa for 15 minutes, than 650 Pa for 15 minutes, then 4000 Pa for 15 minutes, then 150 Pa for 15 minutes, and finally 6300 Pa for 60 minutes.

Such a measurement may also be carried out at varying temperatures, in particular to determine the impact of thermal expansion on the impermeability of the cartridge 2. Thus pressure measurements may be carried out at four different temperatures: 50° C., 15° C., −20° C. and −60° C.

Preferably, a film 72 that is pressure sensitive may be mounted on the ridge 70 of the housing, to determine the spread/distribution of the pressure exerted by the filter cartridge (and more particularly, the gasket seal 6) on the support ridge 70. Thus, it is possible to measure pressure spread prior to injection of fluid into the sealed chamber, and to increase the forces exerted between the cartridge and the housing when loading the cartridge, for example placing the device on a horizontal plane and placing weight on the cartridge. Alternatively, the film may be left in during the impermeability measures using fluid. At the conclusion of the measurements, the pressure sensitive film is removed and analyzed to determine whether parts of the gasket seal 6 of the cartridge are submitted to insufficient pressure to ensure the required seal.

Figure 2:
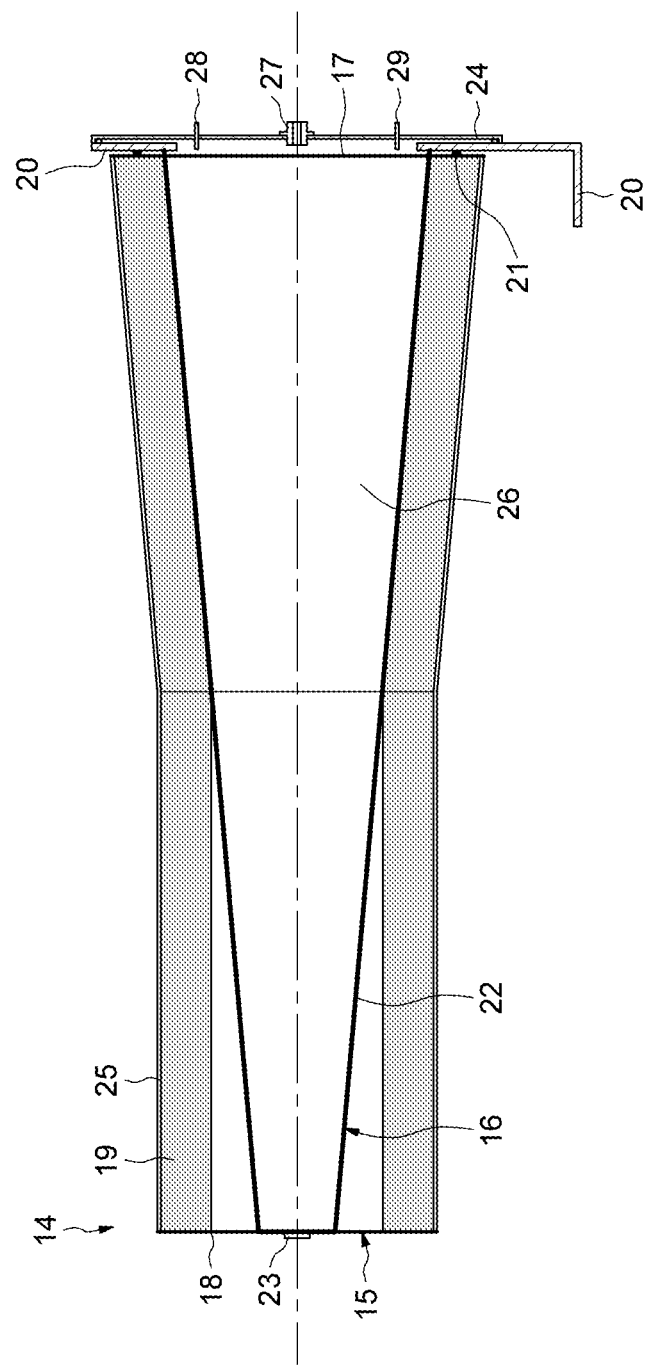
FIG. 2 schematically represents a section of the measuring device according to a second embodiment of the invention, suitable for example for testing filters termed self-cleaning

FIG. 2 schematically represents a section of a measuring device 14 according to a second embodiment of the invention. The device 14 enables measurement of impermeability, in particular to air, of a filter cartridge 15, in particular of the sealing means of the cartridge 15.

The measuring device 14 is suited to cooperate with the cartridge 15 using the attachment means 16. The cartridge 15 comprises a first circular plate 17 presenting an opening that defines an output section, a second circular plate 18 attached at a distance from the first plate 17, and a filter 19 with cylindrical symmetry mounted between the first plate and the second plate. The filter 19 may be a backflushed self-cleaning filter, for example using an air jet, to expel the filter dust, and to reduce losses in capacity when it is functioning. The filter 19, may be cone shaped or cylindrical, and it may consist of pleated filtering material, synthetic or cellulosic. Maintaining the filter's pleating results in a constant filtrating surface during the full service life of the filter. The filter 19 may also be protected on the inside and the outside by (unrepresented) metal or polypropylene mesh.

The measuring device 14 comprises a housing 20 suited to cooperate with the cartridge 15. The housing is attached using the attachment means 16 against the first plate 17, exerting pressure on a seal 21 to ensure a seal between the measuring device 14 and the cartridge 15. The sealing means of cartridge 15 thus comprise the attachment means 16 and the seal 21. The attachment means comprise in particular a tripod 22. The tripod 22 is attached to the housing 20 at the base, and to the second plate 18 at the top, for example using a nut 23. The housing 20 of the measuring device 14 is similar to housing for which the filter cartridge is designed, in view of enabling a test of the impermeability of the sealing means of the cartridge, under conditions similar to those of final usage.

The measuring device 14 also comprises removable means of closure 24 and means of obturation 25. The obturating means 25 are intended to close the filter entry 19, in view of controlling pressure upstream of the cartridge 15. The removable means of closure 24 are suited to cooperate with the housing 20 to form a seal, so that when the cartridge 15 is mounted in the housing 20 using the obturating means 25, a sealed chamber is 26 is created.

The removable means of closure 24, otherwise comprise an entry 27 on which (unrepresented) means of fluid (air or gas) suction or injection may be mounted, for example a pump, in view of increasing or decreasing pressure inside the sealed chamber 26. The removable means of closure 24 may also include a temperature sensor 28 and/or a pressure sensor 29. The temperature sensor 28 enables to determine the temperature of the gas present in the sealed chamber 26, and thus enables to characterize the impermeability of the cartridge depending on temperature of the fluid. The pressure sensor 29 enables to determine changes in pressure, across time, inside the sealed chamber 26.

Thus, the previously described measuring devices enable easy characterization of the impermeability of a filter cartridge, and more specifically impermeability to air of the sealing means. With a housing similar to the one in which the cartridge will be placed for its intended usage, measuring devices reproduce the same conditions of operation and enable to identify at best all eventual leaks at the interfaces of the cartridge and the housing. In particular, the devices may enable to precisely determine the spread of pressure forces exerted between the cartridge and the support. Finally, the measuring devices also enable testing of the consequences of thermal expansion on the filter cartridge and to detect any eventual and resulting leaks.

What is claimed is:

1. A method for measuring the impermeability of a filter cartridge comprising a casing having an input and an output and having a gasket seal coupled to the casing, with a measuring device comprising a housing and a cartridge receiving means configured to cooperate with the gasket seal of the cartridge, the method comprising:
    disposing a pressure sensitive film on the receiving means of the housing;
    positioning the cartridge in the measuring device such that the gasket seal of the cartridge cooperates with the receiving means of the measuring device housing to form a connection between the measuring device and the filter cartridge, and the pressure sensitive film is positioned between the gasket seal and the receiving means;
    blocking an input or an output of the filter cartridge;
    forming a sealed chamber proximate the input or output;
    varying a pressure in the sealed chamber; and
    measuring a change in pressure of the sealed chamber over time to determine the impermeability of the filter cartridge.

2. The method of claim 1, further comprising measuring a temperature of the sealed chamber.

3. The method of claim 1, further comprising varying a temperature in the sealed chamber.

4. The method of claim 1, further comprising measuring the distribution of the pressure exerted on the pressure sensitive film.

5. The method of claim 1, further comprising filling the sealed chamber with a fluid.

6. The method of claim 1, further comprising injecting a visible gas into the sealed chamber.

7. The method of claim 1, wherein forming the sealed chamber proximate the input or output comprises securing a housing unit to a filter cartridge.

* * * * *